(12) United States Patent
Igarashi

(10) Patent No.: US 6,558,819 B1
(45) Date of Patent: May 6, 2003

(54) ARYLSILANE COMPOUND, LIGHT EMITTING DEVICE MATERIAL AND LIGHT EMITTING DEVICE BY USING THE SAME

(75) Inventor: Tatsuya Igarashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 6 days.

(21) Appl. No.: 09/640,275

(22) Filed: Aug. 17, 2000

(30) Foreign Application Priority Data

Aug. 20, 1999 (JP) ............................. 11-234241

(51) Int. Cl.$^7$ ................... H05B 33/14; C09K 11/06; C07F 7/08; C08G 61/12
(52) U.S. Cl. ............... 428/690; 428/447; 428/448; 428/917; 313/504; 257/40; 257/103; 252/301.16; 252/301.35; 556/431; 556/465; 528/25; 528/43
(58) Field of Search ............... 428/690, 917, 428/446, 447, 448; 313/504, 506; 257/40, 103; 252/301.16, 301.35; 556/431, 465, 489; 528/25, 43

(56) References Cited

U.S. PATENT DOCUMENTS

| | | | | |
|---|---|---|---|---|
| 5,807,974 A | * | 9/1998 | Kim et al. | 528/366 |
| 5,876,864 A | * | 3/1999 | Kim et al. | 428/690 |
| 6,232,001 B1 | | 5/2001 | Igarashi | 428/690 |
| 6,307,083 B1 | | 10/2001 | Igarashi | 556/489 |
| 6,310,231 B1 | | 10/2001 | Igarashi et al. | 556/489 |
| 6,338,909 B1 | * | 1/2002 | Kwon et al. | 428/690 |

FOREIGN PATENT DOCUMENTS

| | | | | |
|---|---|---|---|---|
| JP | 6-234968 | | 8/1994 | ........... C09K/11/06 |
| JP | 9-255949 | | 9/1997 | ........... C09K/11/06 |
| JP | 10-265773 | | 10/1998 | ........... C09K/11/06 |
| JP | 11-3781 | | 1/1999 | ........... H05B/33/14 |
| JP | 11-199663 | * | 7/1999 | |

OTHER PUBLICATIONS

Robert J. P. Corriu et al., "Preparation of diphenylsilylene polymers . . . non-linear optical and other properties", Journal of Organometallic Chemistry, vol. 455, pp. 69–76 (1993). (No Month).*

R. D. Miller et al., "Thermally Stable Poly(fluorene) Copolymers for Blue–Light Emission", Nonlinear Optics, vol. 20, pp. 269–295 (1999). (No Month).*

Hwan–Kyu Kim et al, "Novel silicon–containing poly(p–-phenylenevinylene)–related polymers for blue light–emitting diodes", Synthetic Metals 91 (1997) 297–299. (No Month).

* cited by examiner

Primary Examiner—Marie Yamnitzky
(74) Attorney, Agent, or Firm—Sughrue Mion, PLLC

(57) ABSTRACT

A compound containing at least one repeating unit represented by the following formula (1) and at least one repeating unit represented by the following formula (2), a light emitting device material comprising the compound, and a light emitting device containing the light emitting device material:

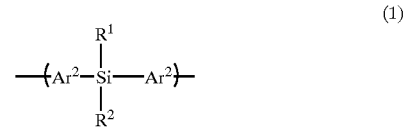

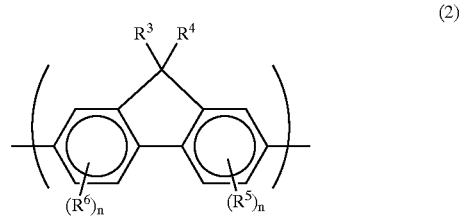

wherein $R^1$ and $R^2$ represent each a substituent; $Ar^1$ and $Ar^2$ represent each an arylene linking group or a heteroarylene linking group; $R^3$ and $R^4$ represent each a hydrogen atom or a substituent; $R^5$ and $R^6$ represent each a substituent; and m and n are each an integer of from 0 to 3.

15 Claims, No Drawings

ARYLSILANE COMPOUND, LIGHT EMITTING DEVICE MATERIAL AND LIGHT EMITTING DEVICE BY USING THE SAME

FIELD OF THE INVENTION

This invention relates to novel silane compounds, light emitting device materials capable of converting electric energy into light thereby emitting light and light emitting devices which are appropriately usable in the fields of, for example, display devices, displays, back lights, electrophotographs, illumination light sources, recording light sources, read light sources, indications, signboards and interiors.

DESCRIPTION OF THE RELATED ART

At present, researches and developments are vigorously made on various display devices. Among all, organic electroluminescence devices have attracted public attention as promising display devices, since they can achieve luminescence at a high luminance even at a low potential. For example, there is known a light emitting device provided with an organic thin film formed by deposition of an organic compound (Applied Physics Letters, Vol. 51, p. 913, 1987). In the light emitting device reported in this document, a tris(8-hydroxyquinolinate) aluminum complex (Alq), which is employed as an electron transport material, is laminated on a hole transport material (an amine compound) to thereby establish largely improved light emitting characteristics compared with the conventional monolayer-type devices.

In an "organic" light emitting device, luminescence at a high luminance can be achieved by laminating organic substances by vacuum deposition. From the viewpoints of the simplification of the production process, processability and enlargement of the area, it is desirable to construct such an device by the coating method. However, devices, in particular, blue-light emitting devices constructed by the conventional coating method are inferior to devices constructed by the deposition method in luminance and luminescence efficiency. Therefore, it has been required to develop a novel blue light emitting material.

SUMMARY OF THE INVENTION

An object of the invention is to provide novel arylsilane compounds, light emitting devices having particularly excellent light emitting characteristics and light emitting device materials enabling the provision of these devices.

This object has been achieved by the following means.

(1) A compound containing at least one repeating unit represented by the following formula (1) and at least one repeating unit represented by the following formula (2):

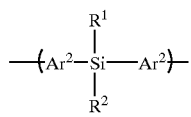
(1)

-continued
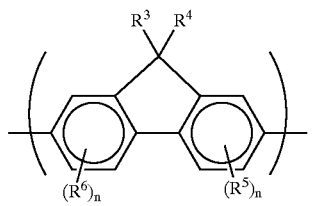
(2)

In the above formulae, $R^1$ and $R^2$ represent each a substituent. $Ar^1$ and $Ar^2$ represent each an arylene linking group or a heteroarylene linking group. $R^3$ and $R^4$ represent each a hydrogen atom or a substituent. $R^5$ and $R^6$ represent each a substituent. m and n are each an integer of from 0 to 3.

(2) The compound as described in the above (1) which has a weight-average molecular weight in terms of polystyrene of from 1,000 to 5,000,000.

(3) The compound as described in the above (1) or (2) which has a fluorescent maximum wavelength λmax of from 400 to 500 nm.

(4) A light emitting device material comprising the compound as described in any of the above (1), (2) and (3).

(5) A light emitting device having a light emitting layer or plural thin organic compound layers comprising a light emitting layer formed between a pair of electrodes, wherein at least one of these layers contains at least one light emitting device material as described in the above (4).

(6) The light emitting device as described in the above (5), wherein a film of the light emitting device material as described in the above (4) is formed by the coating process and the light emitting layer contains at least one light emitting device material as described in the above (4).

DETAILED DESCRIPTION OF THE INVENTION

Now, the invention will be described in greater detail. The compound according to the invention contains at least one repeating unit represented by the formula (1) and at least one repeating unit represented by the formula (2).

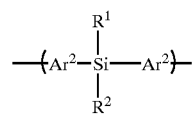
(1)

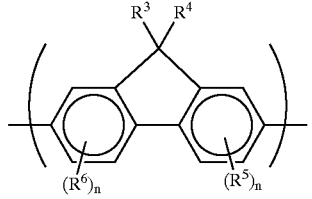
(2)

Now, the formula (1) will be described.

$R^1$ and $R^2$ represent each a substituent. Examples of the substituent include alkyl groups (preferably having from 1 to 30 carbon atoms, still preferably from 1 to 12 carbon atoms and still preferably from 1 to 6 carbon atoms, such as methyl, t-butyl, hexyl and cyclohexyl groups), alkenyl groups (preferably having from 2 to 30 carbon atoms, still preferably from 2 to 12 carbon atoms and still preferably from 2 to 6 carbon atoms, such as propenyl group), alkynyl groups (preferably having from 2 to 30 carbon atoms, still preferably from 2 to 12 carbon atoms and still preferably from 2 to 6 carbon atoms, such as ethynyl group), aryl groups (preferably having from 6 to 40 carbon atoms, still preferably from 6 to 20 carbon atoms and still preferably from 6 to 12 carbon atoms, such as phenyl, naphthyl and anthracenyl group), heteroaryl groups (preferably containing an oxygen atom, a sulfur atom or a nitrogen atom and preferably having from 1 to 40 carbon atoms, still preferably from 2 to 20 carbon atoms and still preferably from 3 to 12 carbon atoms, such as pyridyl, thienyl and carbazolyl groups), alkoxy groups (preferably having from 1 to 30 carbon atoms, still preferably from 1 to 12 carbon atoms and still preferably from 1 to 6 carbon atoms, such as methoxy and isopropoxy groups), aryloxy groups (preferably having from 6 to 40 carbon atoms, still preferably from 6 to 20 carbon atoms and still preferably from 6 to 12 carbon atoms, such as phenoxy, naphthoxy and pyrenyloxy groups), heterocyclic groups (preferably containing an oxygen atom, a sulfur atom or a nitrogen atom and preferably having from 1 to 40 carbon atoms, still preferably from 2 to 20 carbon atoms and still preferably from 3 to 12 carbon atoms, such as piperidyl and morpholino groups), and silyl groups (preferably having from 1 to 30 carbon atoms, still preferably from 3 to 20 carbon atoms and still preferably from 3 to 12 carbon atoms, such as trimethylsilyl, t-butyldimethylsilyl and triphenylsilyl groups). These substituents may have further substituent(s).

It is preferable that $R^1$ and $R^2$ represent each an alkyl, alkenyl, aryl, heteroaryl or alkoxy group, still preferably an alkyl, aryl or heteroaryl group, still preferably an aryl or heteroaryl group, and particularly preferably an aryl group.

$Ar^1$ and $Ar^2$ represent each an arylene group (preferably having from 6 to 40 carbon atoms, still preferably from 6 to 30 carbon atoms and still preferably from 6 to 12 carbon atoms, such as phenylene, naphthalene, anthracenylene or pyrenylene group) or a heteroarylene group (preferably containing either an oxygen atom, a sulfur atom or a nitrogen atom and preferably having from 1 to 50 carbon atoms, still preferably from 1 to 30 carbon atoms and still preferably from 2 to 12 carbon atoms, such as imidazolylene, pyridylene, pyrazylene, furylene, benzazolene (benzoxazolene, benzimidazolylene or benzthiazolylene, preferably benzoxazolene, benzimidazolylene and still preferably benzimidazolylene,) or triazolylene group).

It is preferable that $Ar^1$ and $Ar^2$ represent each an arylene group or a nitrogen-containing heteroarylene group, still preferably an arylene group, still preferably a phenylene group, and particularly preferably an unsubstituted p-phenylene group.

Next, the formula (2) will be described.

$R^3$ and $R^4$ represent each a hydrogen atom or a substituent. Examples of the substituent include alkyl groups (preferably having from 1 to 30 carbon atoms, still preferably from 1 to 20 carbon atoms and particularly preferably from 1 to 10 carbon atoms, such as methyl, ethyl, isopropyl, tert-butyl, n-octyl, n-decyl, n-hexadecyl, cyclopropyl, cyclopentyl and cyclohexyl groups), alkenyl groups (preferably having from 2 to 30 carbon atoms, still preferably from 2 to 20 carbon atoms and particularly preferably from 2 to 10 carbon atoms, such as vinyl, allyl, 2-butenyl and 3-pentenyl groups), alkynyl groups (preferably having from 2 to 30 carbon atoms, still preferably from 2 to 20 carbon atoms and particularly preferably from 2 to 10 carbon atoms, such as propargyl and 3-pentynyl groups), aryl groups (preferably having from 6 to 30 carbon atoms, still preferably from 6 to 20 carbon atoms and particularly preferably from 6 to 12 carbon atoms, such as phenyl, p-methylphenyl, naphthyl and anthranyl groups), amino groups (preferably having from 0 to 30 carbon atoms, still preferably from 0 to 20 carbon atoms and particularly preferably from 0 to 10 carbon atoms, such as amino, methylamino, dimethylamino, diethylamino, dibenzylamino, diphenylamino and ditolylamino groups), alkoxy groups (preferably having from 1 to 30 carbon atoms, still preferably from 1 to 20 carbon atoms and particularly preferably from 1 to 10 carbon atoms, such as methoxy, ethoxy, butoxy and 2-ethylhexyloxy groups), aryloxy groups (preferably having from 6 to 30 carbon atoms, still preferably from 6 to 20 carbon atoms and particularly preferably from 6 to 12 carbon atoms, such as phenyloxy, 1-naphthyloxy and 2-naphthyloxy groups), heteroaryloxy groups (preferably having from 1 to 30 carbon atoms, still preferably from 1 to 20 carbon atoms and particularly preferably from 1 to 12 carbon atoms, such as pyridyloxy, pyrazyloxy, pyrimidyloxy and quinolyloxy groups), acyl groups (preferably having from 1 to 30 carbon atoms, still preferably from 1 to 20 carbon atoms and particularly preferably from 1 to 12 carbon atoms, such as acetyl, benzyl, formyl and pivaloyl groups), alkoxycarbonyl groups (preferably having from 2 to 30 carbon atoms, still preferably from 2 to 20 carbon atoms and particularly preferably from 2 to 12 carbon atoms, such as methoxycarbonyl and ethoxycarbonyl groups), aryloxycarbonyl groups (preferably having from 7 to 30 carbon atoms, still preferably from 7 to 20 carbon atoms and particularly preferably from 7 to 12 carbon atoms, such as phenyloxycarbonyl group), acyloxy groups (preferably having from 2 to 30 carbon atoms, still preferably from 2 to 20 carbon atoms and particularly preferably from 2 to 10 carbon atoms, such as acetoxy and benzoyloxy groups), acylamino groups (preferably having from 2 to 30 carbon atoms, still preferably from 2 to 20 carbon atoms and particularly preferably from 2 to 10 carbon atoms, such as acetylamino and benzoylamino groups), alkoxycarbonylamino groups (preferably having from 2 to 30 carbon atoms, still preferably from 2 to 20 carbon atoms and particularly preferably from 2 to 12 carbon atoms, such as methoxycarbonylamino group), aryloxycarbonylamino groups (preferably having from 7 to 30 carbon atoms, still preferably from 7 to 20 carbon atoms and particularly preferably from 7 to 12 carbon atoms, such as phenyloxycarbonylamino group), sulfonylamino groups (preferably having from 1 to 30 carbon atoms, still preferably from 1 to 20 carbon atoms and particularly preferably from 1 to 12 carbon atoms, such as methanesulfonylamino and benzenesulfonylamino groups) sulfamoyl groups (preferably having from 0 to 30 carbon atoms, still preferably from 0 to 20 carbon atoms and particularly preferably from 0 to 12 carbon atoms, such as sulfamoyl, methylsulfamoyl, dimethylsulfamoyl and phenylsulfamoyl groups), carbamoyl groups (preferably having from 1 to 30 carbon atoms, still preferably from 1 to 20 carbon atoms and particularly preferably from 1 to 12 carbon atoms, such as carbamoyl, methylcarbamoyl, diethylcarbamoyl and phenylcarbamoyl groups), alkylthio groups (preferably having from 1 to 30 carbon atoms, still preferably from 1 to 20 carbon atoms and particularly preferably from 1 to 12 carbon atoms, such as methylthio and ethylthio groups), arylthio groups (preferably having from 6 to 30 carbon atoms, still preferably from 6 to 20 carbon atoms and particularly preferably from 6 to 12 carbon atoms, such as phenylthio group), heteroarylthio groups (preferably having from 1 to 30 carbon atoms, still preferably from 1 to 20 carbon atoms and particularly preferably from 1 to 12 carbon atoms, such as pyridylthio, 2-benzimidazolylthio, 2-benzoxazolylthio and 2-benzthiazolylthio groups), sulfonyl groups (preferably having from 1 to 30 carbon atoms, still preferably from 1 to 20 carbon atoms and particularly preferably from 1 to 12 carbon atoms, such as mesyl and tosyl groups), sulfinyl groups (preferably having from 1 to 30 carbon atoms, still preferably from 1 to 20 carbon atoms and particularly preferably from 1 to 12 carbon atoms, such as methanesulfinyl and benzenesulfinyl groups), ureido groups (preferably having from 1 to 30 carbon atoms, still preferably from 1 to 20 carbon atoms and particularly preferably from 1 to 12 carbon atoms, such as ureido, methylureido and phenylureido groups), phosphonamido groups (preferably having from 1 to 30 carbon atoms, still preferably from 1 to 20 carbon atoms and particularly preferably from 1 to 12 carbon atoms, such as diethylphosphonamido and phenylphosphonamido groups), a hydroxy group, a mercapto group, halogen atoms (such as fluorine, chlorine, bromine and iodine atoms), a cyano group, a sulfo group, a carboxyl group, a nitro group, hydroxamate groups, a sulfino group, a hydrazino group, an imino group, heterocyclic groups (preferably having from 1 to 30 carbon atoms and still preferably from 1 to 12 carbon atoms and having, for example, a nitrogen atom, an oxygen atom or a sulfur atom as the heteroatom, such as imidazolyl, pyridyl, quinolyl, furyl, thienyl, piperidyl, morpholino, benzoxazolyl, benzimidazolyl and benzthiazolyl groups), and silyl groups (preferably having from 3 to 40 carbon atoms, still preferably from 3 to 30 carbon atoms and particularly preferably from 3 to 24 carbon atoms, such as trimethylsilyl and triphenylsilyl groups). These substituents may have further substituent(s).

It is preferable that $R^3$ and $R^4$ represent each a hydrogen atom, an alkyl group, an aryl group, a heteroaryl group or an alkoxy group, still preferably a hydrogen atom or an alkyl group, and still preferably an alkyl group.

$R^5$ and $R^6$ represent each a substituent. Examples of the substituent include those cited above with respect to $R^3$. It is preferable that $R^5$ and $R^6$ represent each an alkyl group, an alkenyl group, an aryl group, a heteroaryl group or an alkoxy group, still preferably an alkyl group or an aryl group, and still preferably an alkyl group.

m and n are each an integer of from 0 to 3. When m and n are each 2 or more, $R^5$'s and $R^6$'s may be either the same or different. It is preferable that m and n are each 0 or 1 and still preferably 0.

It is preferable that the compound according to the invention has at least two, still preferably at least four, repeating units represented by the formula (1). It is also preferable that the compound according to the invention has at least two, still preferably at least four, repeating units represented by the formula (2).

Although the compound of the invention may have the repeating units of the formulae (1) and (2) either in the main chain or in side chains, it is preferable that the repeating units of the formulae (1) and (2) are carried on the main chain.

It is preferable that the weight-average molecular weight (in terms of polystyrene) of the compound according to the invention ranges from 1,000 to 5,000,000, still preferably from 2,000 to 1,000,000 and still preferably from 3,000 to 100,000.

It is preferable that the λmax (the maximum light emitting wavelength) of the fluorescent spectrum of the compound according to the invention ranges from 400 to 500 nm, still preferably from 400 to 480 nm and still preferably from 400 to 460 nm.

The mole ratio of the repeating unit of formula (1) to the repeating unit of formula (2) is not particularly limited, but is preferably 1/20 to 20/1, more preferably 1/10 to 10/1.

The compound of the present invention may have a repeating unit other than the repeating units of formulas (1) and (2). While the repeating unit other than those of formulas (1) and (2) is not particularly limited, examples thereof include an arylene group, a heteroarylene group, a vinylene group, an alkylene group and —X—, wherein X is an oxygen atom, a sulfur group, NH, or a nitrogen atom having a substituent. The compound of the present invention preferably contain 50 mol % to 100 mol % of the repeating units of formulas (1) and (2).

Next, examples of the compound of the present invention will be shown, though the invention is not restricted thereto.

(1-1)

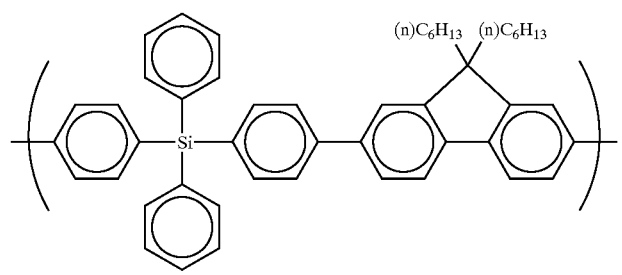

Mw = 6900
(in terms of polystyrene)

(1-2)

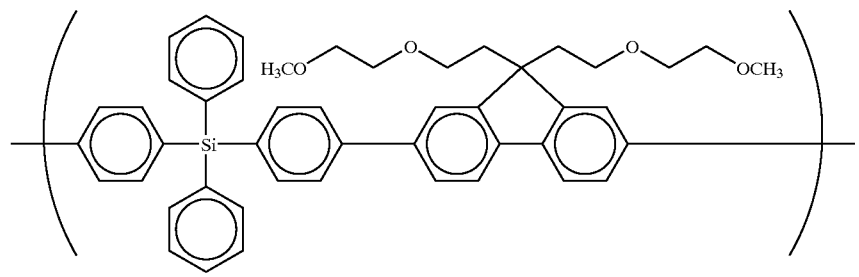

Mw = 9700

-continued
(1-3)
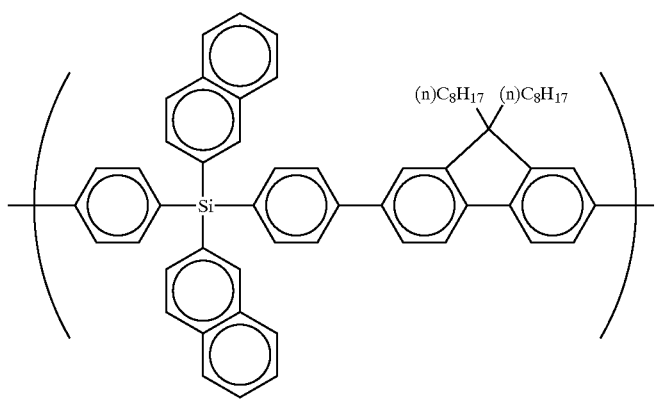
Mw = 9100
(1-4)
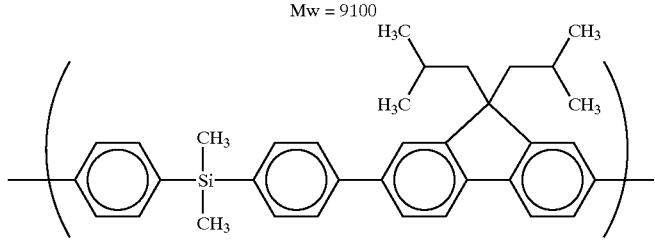
Mw = 4100
(1-5)
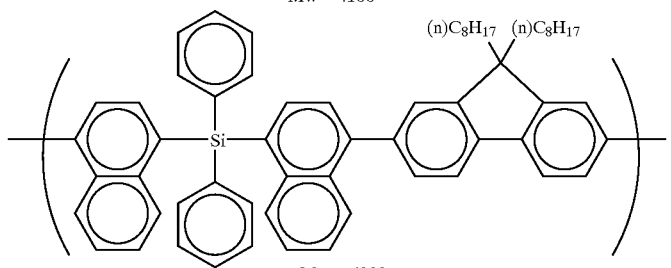
Mw = 6800
(1-6)
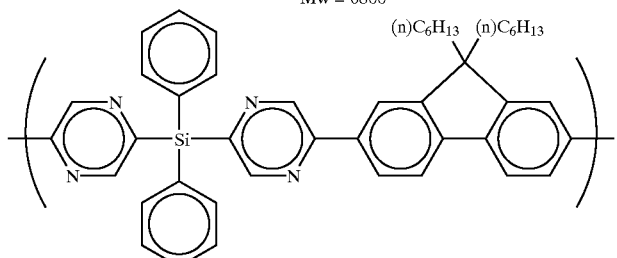
Mw = 3000
(1-7)
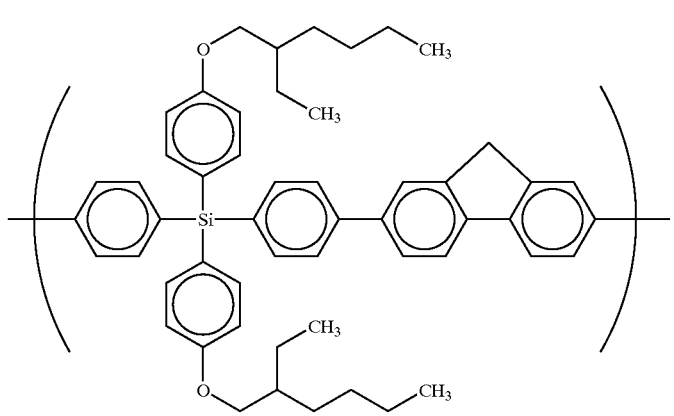
Mw = 4300

-continued
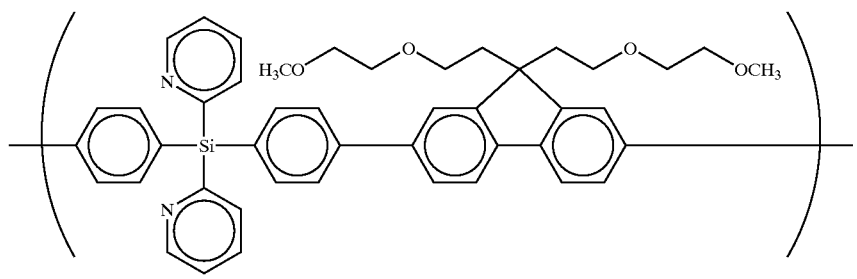
(1-8)
Mw = 5200
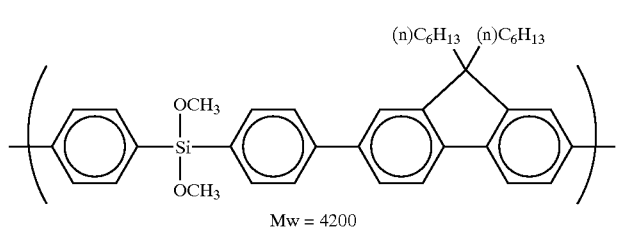
(1-9)
Mw = 4200
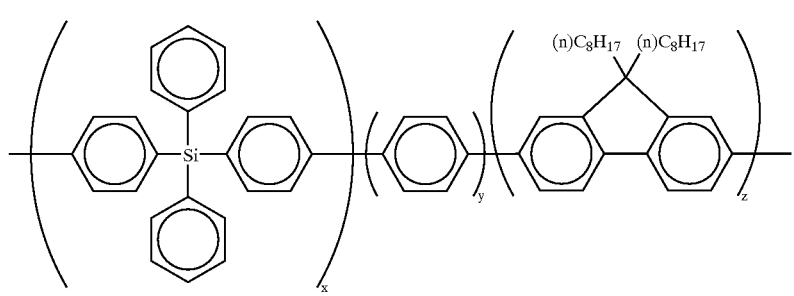
(1-10)
mol ratio
x/y/z = 2/1/1
Mw = 9800
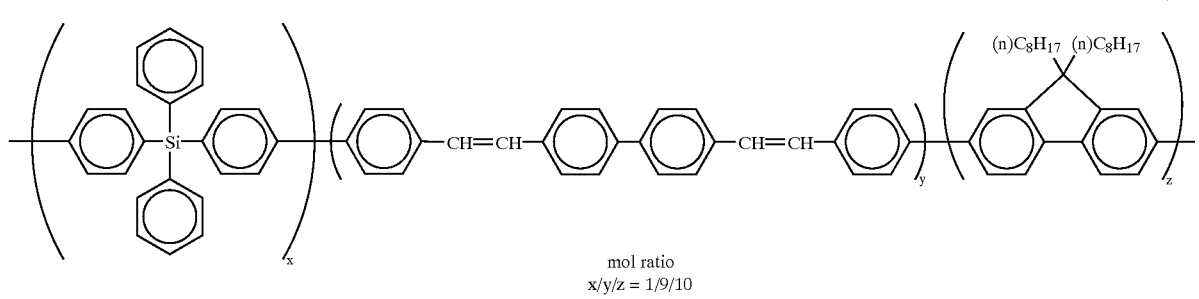
(1-11)
mol ratio
x/y/z = 1/9/10
Mw = 8700
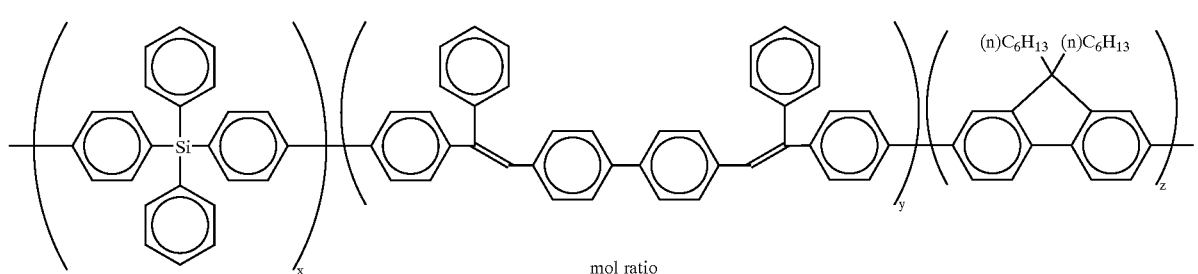
(1-12)
mol ratio
x/y/z = 3/7/10
Mw = 8900

Now, processes for producing the compound according to the invention will be described. The compound of the invention can be synthesized by various processes which have been well known in the art. Examples of these processes include a synthesis (polymerization) process wherein an aryl halide is homo-coupled in the presence of a nickel or copper derivative to form a carbon-carbon bond; a synthesis (polymerization) process wherein an aryl halide derivative is reacted with a vinylbenzene derivative in the presence of a palladium catalyst to form a carbon-carbon bond; a polymerization process wherein a boric acid derivative or a boric acid ester derivative is reacted and coupled with an aryl halide derivative or an aryl triflate derivative in the presence of a palladium catalyst to form a carbon-carbon bond; and a synthesis (polymerization) process wherein alkyl halide derivatives are reacted with each other in the presence of a base to form a carbon-carbon bond. It is preferable to use a synthesis (polymerization) process wherein a carbon-carbon bond is formed in the presence of a palladium catalyst. It is still preferable to use the process wherein a boric acid derivative is polymerized with an aryl halide derivative in the presence of a palladium catalyst.

Examples of the boric acid derivative include optionally substituted arylboric acid derivatives (for example, 1,4-phenyldiboric acid and 4,4'-biphenyldiboric acid) and heteroarylboric acid derivatives (for example, pyridyldiboric acid). Examples of the boric acid ester derivatives include optionally substituted arylboric acid ester derivatives (for example, pinacol phenyldiborate) and heteroarylboric acid ester derivatives (for example, pinacol pyridyldiborate).

It is preferable that the aryl halide derivatives have a chlorine, bromine or iodine atom as the halogen atom and a bromine atom is particularly preferable. Examples of the aryl halide derivatives include dibromobenzene derivatives and dibromobiphenyl derivatives. Examples of the aryl triflate derivatives include ditrifluoromethanesulfonylbenzene derivatives.

Examples of the palladium catalyst include palladium tetrakistriphenylphosphine, palladium carbon, palladium acetate and palladium dichloride (dppf) (dppf: 1,1'-bisdiphenylphosphinoferrocene), though the invention is not restricted thereto. It is also possible to add a ligand such as triphenylphosphine at the same time.

It is preferable to use a base in this reaction. Examples of the base to be used include sodium carbonate, sodium acetate and triethylamine, though the invention is not restricted thereto. It is preferable to use the base in an amount of from 0.1 to 20 equivalents, particularly preferably from 1 to 10 equivalents, to the boric acid (ester) site, though the invention is not restricted thereto.

It is preferable to use a solvent in this reaction. Examples of the solvent to be used include ethanol, water, ethylene glycol dimethyl ether, diethylene glycol dimethyl ether, dimethylformamide, toluene, tetrahydrofuran and mixtures thereof, though the invention is not restricted thereto.

Next, a light emitting device containing the compound according to the invention will be illustrated. The light emitting device of the invention is not particularly restricted in, for example, system, driving method or application mode, so long as it is a device with the use of the compound of the invention. It is preferable that, in the light emitting device of the invention, luminescence by the compound of the invention is utilized or the compound is employed as an electron transport material. As a typical example of the light emitting device, an organic electroluminescence (EL) device can be cited.

In the light emitting device, an organic layer containing the compound of the invention may be formed by, for example, the resistance heat deposition method, the electron beam method, the sputtering method, the molecular lamination method, the coating method or the ink jet method, though the invention is not restricted thereto. Considering the characteristics and production, it is preferable to use the resistance heat deposition method or the coating method, and the coating method is still preferred.

The light emitting device according to the invention is a device having a light emitting layer or plural thin organic compound films involving a light emitting layer formed between a pair of electrodes, i.e., an anode and a cathode. In addition to the light emitting layer, it may have, for example, a hole injection layer, a hole transport layer, an electron injection layer, an electron transport layer and a protective layer. Each of these layers may have other function(s). Each layer may be formed by using various materials.

As the anode which supplies holes to, for example, the hole injection layer, the hole transport layer and the luminescence layer, use may be made of metals, alloys, metal oxides, electrically conductive compounds or mixtures thereof. It is preferable to use a material having a work function of 4 eV or above. Particular examples thereof include conductive metal oxides such as tin oxide, zinc oxide, indium oxide and indium tin oxide (ITO), metals such as gold, silver, chromium and nickel, mixtures or laminates of these metals and conductive metal oxides, inorganic conductive materials such as copper iodide and copper sulfide, organic conductive materials such as polyaniline, polythiophene and polypyrrole, and laminates of these materials with ITO. It is preferable to use conductive metal oxides. Among all, ITO is particularly preferable from the viewpoints of productivity, conductivity and transparency. Although the film thickness of the anode can be appropriately selected depending on the material employed, it preferably ranges from 10 nm to 5 $\mu$m, still preferably from 50 nm to 1 $\mu$m and still preferably from 100 nm to 500 nm.

It is a practice to construct an anode by forming layers on a substrate made of, for example, soda lime glass, no-alkali glass or a transparent resin. In case of using glass, it is preferable to use no-alkali glass so as to minimize ions eluted from the glass. In case of using soda lime glass, it is preferable to provide a barrier coating made of, for example, silica. The thickness of the substrate is not particularly restricted, so long as it is sufficient for maintaining the adequate mechanical strength. In case of using glass, the substrate thickness is usually at least 0.2 mm, preferably at least 0.7 mm.

The anode may be constructed by various methods appropriately selected depending on the material. In case of using ITO, for example, a film is formed by the electron beam method, the sputtering method, the resistance heat deposition method or the chemical reaction method (for example, the sol-gel method) or by applying a dispersion of indium tin oxide.

The anode may be subjected to further treatments such as washing so as to lower the driving voltage of the device or elevate the luminescence efficiency. In case of ITO, for example, it is effective to perform UV-ozone treatment or plasma treatment.

The cathode, which supplies electrons to, for example, the electron injection layer, the electron transport layer and the luminescent layer, is selected by taking into consideration the adhesiveness to the layers (for example, the electron injection layer, the electron transport layer and the luminescent layer) adjacent to the negative electrode, ionization potential and stability. As the cathode material, use can be made of metals, alloys, metal halides, metal oxides, electrically conductive compounds and mixtures thereof. Particular examples thereof include alkali metals (for example, Li, Na and K) and fluorides thereof, alkaline earth metals (for example, Mg and Ca) and fluorides thereof, gold, silver, lead, aluminum, sodium-potassium alloy and mixtures of these metals, lithium-aluminum alloy and mixtures of these metals, magnesium-silver alloy and mixtures of these metals, and rare earth metals such as indium and ytterbium. It is preferable to use a metal having a work function of 4 eV or below. It is still preferable to use aluminum, lithium-aluminum alloy or a mixture of these metals, magnesium-silver alloy or a mixture of these metals. The cathode may have either a single-layer structure made of such a compound or mixture as cited above or a laminated structure containing the compound or mixture. Although the film thickness of the cathode can be appropriately selected depending on the material employed, it preferably ranges from 10 nm to 5 μm, still preferably from 50 nm to 1 μm and still preferably from 100 nm to 1 μm.

To construct the cathode, it is possible to employ, for example, the electron beam method, the sputtering method, the resistance heat deposition method or the coating method. A single metal may be deposited. Alternatively, it is possible to deposit two or more components simultaneously. It is also possible to deposit plural metals simultaneously to thereby form an alloy electrode. Furthermore, it is possible to deposit an alloy having been preliminarily prepared.

The lower sheet resistance of the anode and the cathode is the more favorable. That is to say, it is preferable that the sheet resistance is several hundred Ω/□ or less.

The light emitting layer may be made of an arbitrary material, so long as it enables the formation of a layer having a function of, at the application of an electric field, injecting holes from the anode, the hole injection layer or the hole transport layer and a function of injecting electrons from the cathode, the electron injection layer or the electron transport layer, a function of transferring the thus injected charge, and a function of allowing the formation of hole-electron bond again. For example, use can be made of benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes typified by metal complexes and rare earth element complexes of 8-quinolinol derivatives, polymer compounds such as polythiophene, polyphenylene and polyphenylenevinylene, organosilane derivatives and the compounds according to the invention. Although the film thickness of the light emitting layer is not particularly restricted, it preferably ranges from 1 nm to 5 μm, still preferably from 5 nm to 1 μm and still preferably from 10 nm to 500 nm.

The light emitting layer may be formed by, for example, the resistance heat deposition method, the electron beam method, the sputtering method, the molecular lamination method, the coating method (for example, the spin-coating method and the dip-coating method), the ink jet method or the LB method, though the invention is not restricted thereto. Among all, it is preferable to employ the resistance heat deposition method or the coating method.

The hole injection layer and the hole transport layer may be made of an arbitrary material, so long as it has a function of injecting holes from the anode, a function of transporting holes or a barrier function against electrons injected from the cathode. Particular examples thereof include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, aniline-based copolymers, conductive high-molecular weight oligomers such as thiophene oligomer and polythiophene, organosilane derivatives and the compounds according to the invention. Although the film thickness of the hole injection layer or the hole transport layer is not particularly restricted, it preferably ranges from 1 nm to 5 μm, still preferably from 5 nm to 1 μm and still preferably from 10 nm to 500 nm. The hole injection layer or the hole transport layer may have either a single-layer structure made of one or more materials as cited above or a laminated structure consisting of two or more layers having the same or different compositions.

The hole injection layer and the hole transport layer may be formed by, for example, the vacuum deposition method, the LB method, the coating method (for example, the spin-coating method, the casting method and the dip-coating method) wherein the hole injection/transport material as described above is dissolved or dispersed in a solvent and subjected to coating, or the ink jet method. In case of the coating method, the hole injection/transport material can be dissolved or dispersed together with a resin component. Examples of the resin component include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethyl cellulose, vinyl acetate, ABS resins, polyurethane, melamine resins, unsaturated polyester resins, alkyd resins, epoxy resins and silicone resins.

The electron injection layer and the electron transport layer may be made of an arbitrary material, so long as it has a function of injecting electrons from the cathode, a function of transporting electrons or a barrier function against holes injected from the anode. Particular examples thereof include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, heterocyclic tetracarboxlic acid anhydrides such as napthaleneperylene derivatives, various metal complexes typified by metal complexes of 8-quinolinol derivatives and metal complexes having metal phthalocyanine, benzoxazole or benzothiazole as a ligand, organosilane derivatives the compounds according to the invention. Although the film thickness of the electron injection layer or the electron transport layer is not particularly restricted, it preferably ranges from 1 nm to 5 μm, still preferably from 5 nm to 1 μm and still preferably from 10 nm to 500 nm. The electron injection layer or the electron transport layer may have either a single-layer structure made of one or more materials as cited above or a laminated structure consisting of two or more layers having the same or different compositions.

The electron injection layer and the electron transport layer may be formed by, for example, the vacuum deposition method, the LB method, the coating method (for example, the spin-coating method, the casting method and the dip-coating method) wherein the electron injection/transport material as described above is dissolved or dispersed in a solvent and subjected to coating, or the ink jet method. In case of the coating method, the electron injection/transport material can be dissolved or dispersed together with a resin component. Examples of the resin component include those cited above with respect to the hole transport layer.

The protective layer may be made of an arbitrary material, so long as it has a function of preventing the invasion of substances promoting the deterioration of the device (for example, moisture and oxygen) into the device. Particular examples thereof include metals (for example, In, Sn, Pb, Au, Cu, Ag, Al, Ti and Ni), metal oxides (for example, MgO, SiO, $SiO_2$, $Al_2O_3$, GeO, NiO, CaO, BaO, $Fe_2O_3$, $Y_2O_3$ and $Ti_2O_3$), metal fluorides (for example, $MgF_2$, LiF, $AlF_3$ and $CaF_2$), polyethylene, polypropylene, polymethyl methacrylate, polyimide, polyurea, polytetrafluoroethylene, polychlorotrifluoroethylene, polydichlorodifluoroethylene, chlorotrifluoroethylen-dichlorodifluoroethylene copolymer, copolymers obtained by copolymerizing tetrafluoroethylene with a monomer mixture containing at least one comonomer, fluorinated copolymers having a cyclic structure in the main copolymer chain, water-absorptive materials having a water absorptivity of at least 1%, and moisture-proof materials having a water absorptivity of 0.1% or less.

The protective layer may be formed by an arbitrary method without restriction. For example, use can be made of the vacuum deposition method, the sputtering method, the reactive sputtering method, the MBE (molecular beam epitaxy) method, the cluster ion beam method, the ion plating method, the plasma-polymerization method (the high-frequency excitation ion plating method), the plasma CVD method, the laser CVD method, the heat CVD method, the gas source CVD method or the coating method.

EXAMPLES

Now, the invention will be described in greater detail by reference to the following Examples. However, it is to be understood that the invention is not construed as being limited thereto.

Synthesis of Compound (1-1)

20 ml of diethylene glycol dimethyl ether was added to 0.87 g of bisbromophenyldiphenylsilane a, 1.0 g of bisboric acid pinacol ester derivative 0.75 g of sodium carbonate, 0.14 g of triphenylphosphine and 0.05 g of palladium carbon and the mixture was stirred under reflux. After 8 hours, the liquid reaction mixture was diluted with 200 ml of chloroform and 200 ml of water and filtered through celite. The organic layer was washed with 200 ml portions of water twice and dried over sodium sulfate. After concentrating the solvent, 300 ml of methanol was added to the residue and the solid thus precipitated was collected by filtration. Thus 1.2 g of a white solid product (1-1) was obtained. When analyzed by GPC, it had a molecular weight (Mw) of 6,900 in terms of polystyrene. 40 mg of the product (1-1) was dissolved in 3 ml of dichloroethane and the resultant solution was subjected to spin-coating at 2,000 rpm for 10 seconds. The thin film thus formed had a fluorescent maximum wavelength λmax of 403 nm.

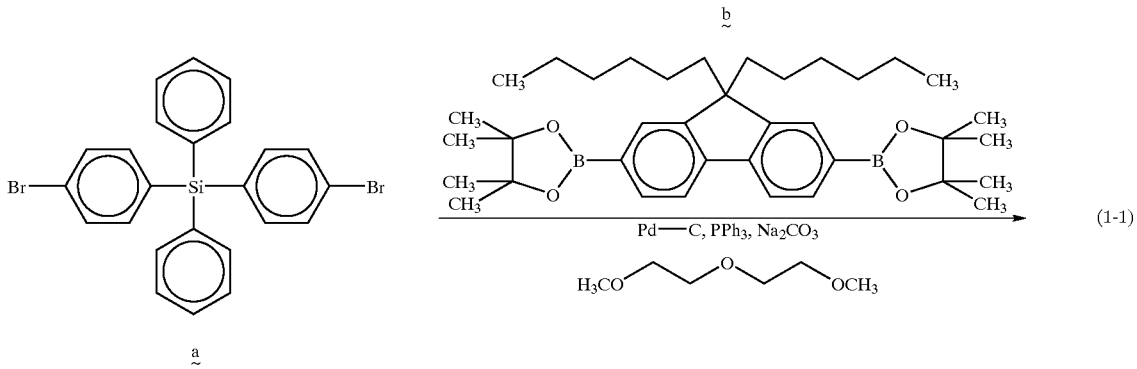

Comparative Example 1

Baytron P (PEDOT-PPS solution (polydioxyethylene thienylene-polystyrenesulfonic acid dope), manufactured by Bayer A. G.) was spin-coated on a washed ITO substrate at 2,000 rpm for 60 seconds and then vacuum-dried at 100° C. for 1 hour to form a hole transport film (film thickness: about 40 nm). 40 mg of the compound c (Mw=6,300) was dissolved in 3 ml of dichloroethane and then spin-coated (2,000 rpm, 20 seconds) on the PEDOT-PSS layer formed previously. A patterned mask (a mask giving a light emitting area of 4 mm×5 mm) was provided on the organic thin film and magnesium and silver (10:1) were co-deposited to give a thickness of 50 nm in a deposition chamber. Subsequently, silver (50 nm) was deposited. A DC constant potential was applied on the EL device by using a source measure unit (Model 2400, manufactured by Toyo Technica) and the luminance thus achieved was measured by using a luminance meter (Model BM-8, manufactured by TOPCON) while the light emitting wavelength was measured by using a spectrum analyzer (Model PMA-11, manufactured by Hamamatsu Photonics). As a result, bluish green luminescence of a chromaticity (0.19, 0.22) was obtained and the luminance was 122 $cd/m^2$ at 11 V.

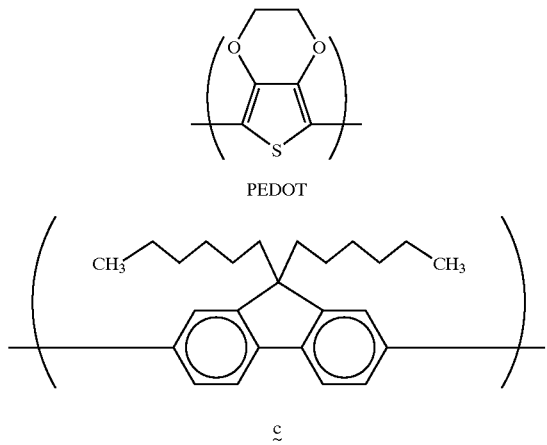

c

Example 1

A device was constructed and evaluated as in Comparative Example 1 but using the compound (1-1) of the invention as a substitute for the compound c. As a result, blue luminescence with a high color purity of a chromaticity (0.14, 0.10) was obtained and the luminance was 310 cd/m² at 13 V.

Example 2

A device was constructed and evaluated as in Comparative Example 1 but using the compound (1-11) of the invention as a substitute for the compound c. As a result, blue luminescence with a high color purity of a chromaticity (0.15, 0.15) was obtained and the luminance was 660 cd/m² at 13 V.

Example 3

40 mg of poly(N-vinylcarbazole) and 12 mg of the compound (1-12) were dissolved in 4 ml of 1,2-dichloroethane and the resultant solution was spin-coated on a washed ITO substrate. The organic thin film thus formed has a film thickness of about 70 nm. On this film, the compound d was deposited to give a thickness of 40 nm and a cathode was further deposited thereon as in Comparative Example 1. The thus constructed device was evaluated as in Comparative Example 1. As a result, blue luminescence of a chromaticity (0.15, 0.16) was obtained and the luminance was 1,090 cd/m² at 10 V.

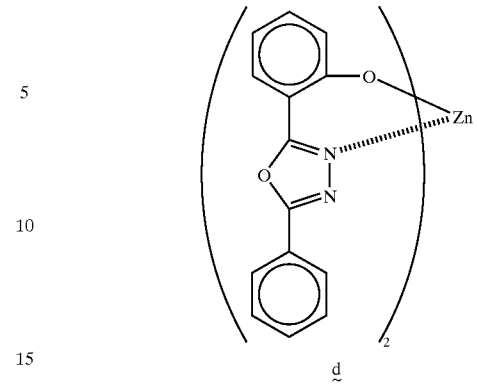

d

By constructing and evaluating EL devices containing the compounds of the invention in the same manner, it can be confirmed that the compounds of the invention function as EL materials. It is also found out that blue light emitting devices with a high color purity can be thus obtained.

The compounds according to the invention are usable as organic EL materials. The devices containing the compounds of the invention are excellent in EL characteristics such as hue. Moreover, the compounds of the invention are applicable to, for example, medical purposes, fluorescent brighteners, photographic materials, UV-absorbing materials, laser pigments, color filter dyes and color change filters.

The entire disclosure of each and every foreign patent application from which the benefit of foreign priority has been claimed in the present application is incorporated herein by reference, as if fully set forth.

What is claimed is:

1. A compound comprising at least two units represented by the following formula (1) and at least two units represented by the following formula (2):

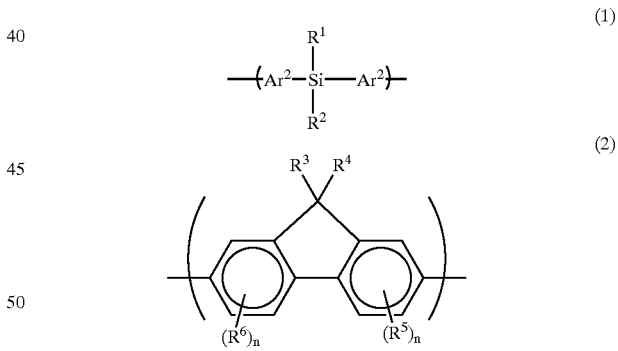

wherein $R^1$ and $R^2$ each independently represents an aryl group or a heteroaryl group; $Ar^1$ and $Ar^2$ each independently represents an arylene linking group or a heteroarylene linking group; $R^3$ and $R^4$ each independently represents a hydrogen atom or a substituent; $R^5$ and $R^6$ each independently represents a substituent; and m and n are each an integer of from 0 to 3.

2. The compound of claim 1, wherein $R^1$ and $R^2$ each represents an aryl group.

3. The compound of claim 1, wherein $Ar^1$ and $Ar^2$ each represents an arylene group when $R^1$ and $R^2$ each represents an aryl group.

4. The compound of claim 1, wherein $Ar^1$ and $Ar^2$ each represents an arylene group when $R^1$ and $R^2$ each represents a heteroaryl group.

5. The compound of claim 1, wherein $R^1$ and $R^2$ each represents a heteroaryl group.

6. The compound of claim 1, wherein $Ar^1$ and $Ar^2$ each represents a heteroarylene group when $R^1$ and $R^2$ each represents an aryl group.

7. The compound of claim 1, wherein $Ar^1$ and $Ar^2$ each represents a heteroarylene group when $R^1$ and $R^2$ each represents a heteroaryl group.

8. A light emitting device comprising at least one organic layer including a light emitting layer between a pair of electrodes, wherein said at least one organic layer comprises at least one compound comprising at least two units represented by the following formula (1) and at least two units represented by the following formula (2):

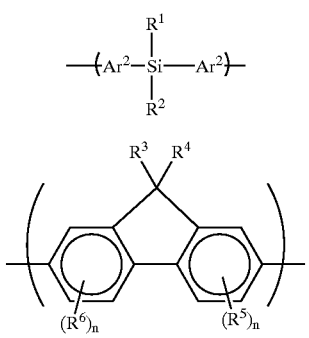

wherein $R^1$ and $R^2$ each independently represents an aryl group or a heteroaryl group; $Ar^1$ and $Ar^2$ each independently represents an arylene linking group or a heteroarylene linking group; $R^3$ and $R^4$ each independently represents a hydrogen atom or a substituent; $R^5$ and $R^6$ each independently represents a substituent; and m and n are each an integer of from 0 to 3.

9. The light emitting device of claim 8, wherein $R^1$ and $R^2$ each represents an aryl group.

10. The light emitting device of claim 8, wherein $Ar^1$ and $Ar^2$ each represents an arylene group when $R^1$ and $R^2$ each represents an aryl group.

11. The light emitting device of claim 8, wherein $Ar^1$ and $Ar^2$ each represents an arylene group when $R^1$ and $R^2$ each represents a heteroaryl group.

12. The light emitting device of claim 8, wherein $R^1$ and $R^2$ each represents a heteroaryl group.

13. The light emitting device of claim 8, wherein $Ar^1$ and $Ar^2$ each represents a heteroarylene group when $R^1$ and $R^2$ each represents an aryl group.

14. The light emitting device of claim 8, wherein $Ar^1$ and $Ar^2$ each represents a heteroarylene group when $R^1$ and $R^2$ each represents a heteroaryl group.

15. The light emitting device of claim 8, wherein said at least one organic layer is formed by a coating process.

* * * * *